United States Patent [19]

Biere et al.

[11] Patent Number: 5,700,808
[45] Date of Patent: *Dec. 23, 1997

[54] 5- OR 6-SUBSTITUTED β-CARBOLINE-3-CARBOXYLIC ACID ESTERS

[75] Inventors: Helmut Biere; Andreas Huth; Dieter Rahtz; Ralph Schmiechen; Dieter Seidelmann; Wolfgang Kehr; Herbert Hans Schneider, all of Berlin, Germany; Mogens Engelstoft, Vaerløse, Denmark; Bondo John Hansen, Lyngby, Denmark; Frank Waetjen, Bajsvaerd, Denmark; Tage Honoré, Maaloev, Denmark

[73] Assignee: Schering Aktiengesellschaft, Berlin, Germany

[*] Notice: The term of this patent shall not extend beyond the expiration date of Pat. No. 5,414,002.

[21] Appl. No.: 245,278

[22] Filed: May 18, 1994

Related U.S. Application Data

[62] Division of Ser. No. 416,629, Oct. 3, 1989, Pat. No. 5,414,002, which is a continuation of Ser. No. 3,179, Jan. 14, 1987, which is a continuation of Ser. No. 933,435, Nov. 21, 1986, abandoned.

[30] Foreign Application Priority Data

Mar. 2, 1986 [DE] Germany .......... 36 09 699.7

[51] Int. Cl.⁶ .......... A61K 31/44; C07D 471/04
[52] U.S. Cl. .......... 514/292; 546/86
[58] Field of Search .......... 546/86; 514/292

[56] References Cited

U.S. PATENT DOCUMENTS

| | | | |
|---|---|---|---|
| 4,371,536 | 2/1983 | Braestrup et al. | 424/256 |
| 4,435,403 | 3/1984 | Braestrup et al. | 424/256 |
| 4,623,649 | 11/1986 | Huth et al. | 514/292 |
| 4,731,365 | 3/1988 | Biere et al. | 514/222 |
| 4,757,070 | 7/1988 | Biere et al. | 514/228 |
| 4,778,800 | 10/1988 | Huth et al. | 514/292 |
| 4,894,377 | 1/1990 | Seidelmann | 514/292 |
| 5,071,859 | 12/1991 | Knudsen | 514/326 |

FOREIGN PATENT DOCUMENTS 130140   1/1985   European Pat. Off.

OTHER PUBLICATIONS

Loscher "Comparative assay of auticonvulsant and toxic potencies of 16 GABAmimetic drugs" Index Medicus 83:013275 (1982).
Speeg et al "In Vito Antagonism of Benzodiazepine Binding" Index Medicus 81:095339 (1981).
Leeb-Lundberg et al "Barbiturate Receptor Sites are Coupled to Benzodiazepine Receptors" Index Medicus 81:175171 (1981).
Shanon et al "β-Carboline-3 Carboxylate-T-Butyl Esters" Life Science, 35 2227-2236 (1984).
Codding et al "Structure Activity Studies of β-Carbolines" Can. J. Chem. 66 2981-2988 (1988).
Clark et al "Principles of Psychopharmacology" Academic Press, 1970, pp. 166-167.
Goto et al "The Role of Receptors in Biology and Medicine" Raven Press 1987, p. 191.

*Primary Examiner*—Ceila Chang
*Attorney, Agent, or Firm*—Millen, White, Zelano, & Branigan, P.C.

[57] ABSTRACT

5- or 6-substituted β-carboline-3-carboxylic acid esters of Formula I

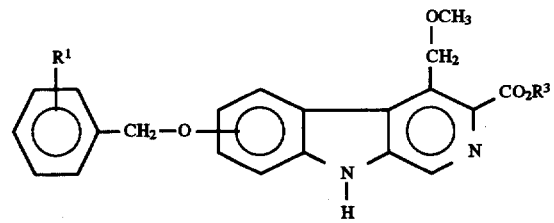

wherein
$R^1$ is hydrogen, nitrilo, halogen, lower alkyl or lower alkoxy, and
$R^3$ is a branched $C_{3-6}$ alkyl group which is optionally substituted by halogen, or a $C_{3-6}$ cycloalkyl group which is optionally methyl-substituted, are valuable pharmaceuticals.

9 Claims, No Drawings

5- OR 6-SUBSTITUTED β-CARBOLINE-3-CARBOXYLIC ACID ESTERS

This is a division of application Ser. No. 07/416,629 filed Oct. 3, 1989, which in turn is a continuation of application Ser. No. 003,179, of Jan. 14, 1987, which is a continuation of Ser. No. 06,933,435 filed Nov. 21, 1986 abandoned.

BACKGROUND OF THE INVENTION

This invention relates to novel 5- or 6-substituted β-carboline-3-carboxylic acid esters.

Numerous patents have described β-carboline-3-carboxylic acid esters, for example, EP Patent 30,254 which discloses the β-carboline-3-carboxylic acid isopropyl ester and the β-carboline-4-ethyl-3-carboxylic acid isopropyl ester; DOS 3,332,895 which describes the 5-[1-(4-chlorophenyl)-ethoxy-4-methoxymethyl-β-carboline-3-carboxylic acid isopropyl ester (See U.S. Ser. No. 623,610, of Jun. 22, 1984); and U.S. Pat. No. 4,435,403, relating to the 5-benzyloxy- and 6-benzyloxy-4-methoxymethyl-β-carboline-3-carboxylic acid esters. These references further disclose genera which generically overlap a portion of the genera of this application. All of these references are entirely incorporated by reference herein. It can be seen from these that β-carboline-3-carboxylic acid esters affect the central nervous system and are suitable as pharmaceuticals.

β-Carboline-3-carboxylic acid ethyl esters are cleaved with relative ease into the corresponding acid by appropriate enzymes; these acids exhibit no affinity, or only a slight affinity, to benzodiazepine receptors.

SUMMARY OF THE INVENTION

It is thus an object of this invention to provide new compounds having valuable pharmaceutical properties and preferably lacking or ameliorating the prior art drawbacks.

It has now been found surprisingly that the compounds of this invention do not possess this drawback or possess it to a much lower degree and display increased stability with respect to esterases.

The 5- or 6-substituted β-carboline-3-carboxylic acid esters of the present invention have the Formula I

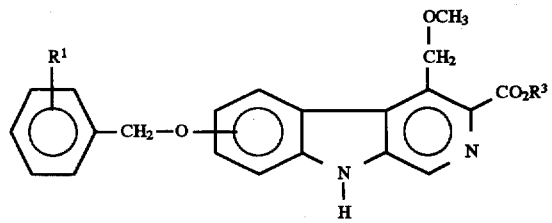

wherein, $R^1$ is hydrogen, nitrilo, halogen, lower alkyl, or lower alkoxy, and $R^3$ is a branched $C_{3-6}$-alkyl group optionally substituted by halogen, or a $C_{3-6}$ cycloalkyl group which is optionally methyl-substituted.

Halogen throughout includes, for example, fluorine, chlorine and bromine; fluorine and chlorine are preferred.

Suitable lower alkyl groups $R^1$ and the alkyl portions of the lower alkoxy groups $R^1$ include those of 1–4 carbon atoms, for example, methyl, ethyl, propyl, isopropyl, butyl, isobutyl, 2-butyl, tert-butyl; lower alkyl groups of 1–2 carbon atoms are preferred. The mono-substituted $R^1$ can be in the 2-, 3-, or 4-position on the phenyl residue; the later can be mono- or polysubstituted (up to 5 times), preferably being mono- or disubstituted.

Branched alkyl groups of 3–6 carbon atoms $R^3$ include, for example, the following secondary and tertiary alkyl groups: isopropyl, tert-butyl, isobutyl, 2-butyl, neopentyl, inter alia. Especially suitable are branched alkyl groups of 3–4 carbon atoms. Typically the number of halo substituents on the alkyl groups will be up to perhalo substitution and usually in the approximate range of 1–6.

Examples of $C_{3-6}$ cycloalkyl groups $R^3$, optionally methyl-substituted, include: cyclopropyl, methylcyclopropyl, cyclobutyl, cyclopentyl, methylcyclopentyl, cyclohexyl, etc. Typically, the ring will be substituted by 1–2 methyl groups.

The effect of the compounds of Formula I on the central nervous system and their instability with respect to esterases were determined by investigations using conventional methods.

As can be seen from the table below, using as example the 6-benzyloxy-4-methoxymethyl-beta-carboline-3-carboxylic acid ispropyl ester (B) in comparison with the conventional 6-benzyloxy-4-methoxymethyl-beta-carboline-3-carboxylic acid ethyl ester (A), the compounds of this invention display superior activities in the in vivo binding test, in the chimney test, and in bioavailability.

| | $ED_{50}$ mg/kg in vivo | Chimney Test $ED_{50}$ (mg/kg) i.p. | Bioavailability Rats % |
| --- | --- | --- | --- |
| A | 5.6 | 12.1 | 17 |
| B | 0.4 | >50 | 32 |

The $ED_{50}$ in vivo value represents the dose of a test compound effecting a reduction in specific binding of flunitrazepam to the benzodiazepine receptor in a living brain to 50% of the control value.

The chimney test was performed according to the method of Poissier, Jr., et al. Med. Exp. 3: 81–84 (1960). The higher the $ED_{50}$ value in the chimney test the better, since this indicates a lower activity in inducing motor discoordination.

The above-mentioned, conventional β-carboline-3-carboxylic acid isopropyl esters exhibit, as compared with the compounds of this invention, a substantially poorer binding capability to the benzodiazepine receptors.

The compounds of general Formula I further exhibit in pharmacological tests superior psychotropic properties and, in particular, superior anxiolytic characteristics, a lesser sedative action also being observed.

The compounds of this invention, based on their valuable pharmacological properties, especially their effect on the central nervous system, thus are suited as psychopharmaceuticals in medicine for administration to mammals including humans.

The compounds can be employed, in particular, for the treatment of anxiety, epilepsy, and sleep disturbances.

Thus, the compounds of this invention can be utilized for the formulation of pharmaceutical preparations, for example for oral and parenteral administration in accordance with conventional methods of galenic pharmacy. Suitable auxiliary materials for the formulation of pharmaceutical preparations are those physiologically compatible, organic and inorganic excipients suitable for enteral and parenteral administration which are inert with respect to the compounds of this invention. Examples of excipients include: water, saline solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydromethylcellulose, and polyvinylpyrrolidone. The pharmaceutical preparations can be sterilized and/or mixed with auxiliary agents, such as lubricants, preservatives, stabilizers, wetting agents, emulsifiers, buffers, and colorants.

Especially suited for parenteral administration are injection solutions or suspensions, especially aqueous solutions of the active compounds in polyhydroxyethoxylated castor oil. However, it is likewise possible to employ physiologically compatible auxiliary surfactants, such as salts of bile acids, or animal and vegetable phospholipids, but also mixtures thereof, as well as liposomes of their components as carrier systems.

For oral administration, particularly suitable are tablets, dragees, or capsules with talc and/or a hydrocarbon excipient or binder, e.g., lactose, cornstarch or potato starch. Use in liquid form is likewise possible, e.g., as an elixir to which a sweetener is optionally added.

The compounds according to this invention are typically introduced into a physiologically compatible excipient in a dosage unit of 0.05–100 mg active compound. The compounds of this invention are typically utilized in a dosage of 0.1–300 mg/day. Their administration is analogous to that of diazepam, e.g, for treatment of sleep disorders and anxiety and to that of clonazepam for treatment of epilepsy.

The preparation of the compounds according to the invention takes place by means of conventional methods.

For example, the compounds of general Formula I can be prepared by (a) reacting a compound of Formula II

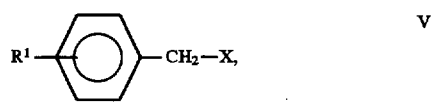

wherein $R^1$ is as defined above, with the corresponding ester of glycinimine of Formula III

wherein $R^3$ is as defined above, $R^5$ is an aromatic group preferably substituted by 4-methoxy or hydrogen, and $R^6$ is hydrogen or optionally an aromatic group, and subsequently cleaving the imine, by hydrolysis, to form the amine of Formula IV

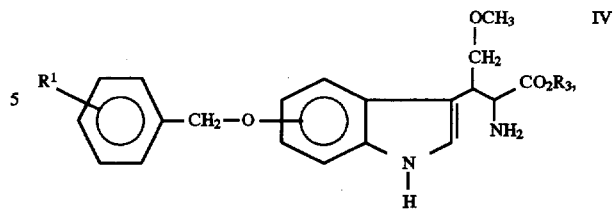

and then cyclizing with formaldehyde or glyoxylic acid wherein the cyclization can also be essentially combined with acid cleavage of the imine as a one-shot reaction; and subsequently aromatizing, and, if desired, splitting off the benzyl group, and thereafter etherifying the thus-obtained free hydroxy group with a compound of Formula V

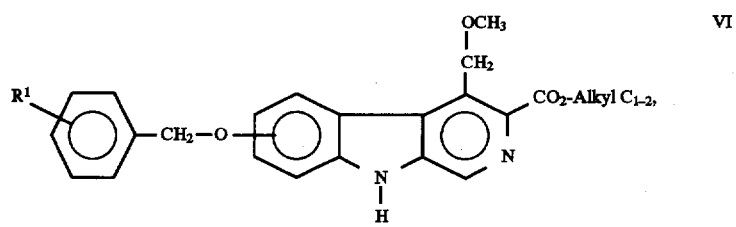

wherein $R^1$ is as defined above and

X is, for example, halogen or tosyl; or (b) interesterifying a compound of Formula VI

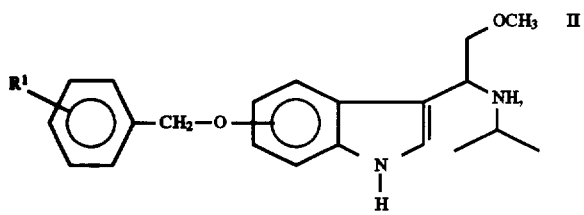

wherein $R^1$ is as defined above.

The substitution according to process version (a) can be performed, for example, by adding the compounds of Formula II in a polar solvent—preferably aprotic, such as, for example, dimethylformamide or N-methylpyrrolidone—optionally with addition of another solvent, e.g., toluene, to a mixture of the imine of Formula III in the same solvent with a base, preferably potassium carbonate, at an elevated temperature, preferably at 90°–105° C., and by reacting at the same temperature.

The subsequent cleavage of the thus-formed imine to the amine can be performed by hydrolysis, preferably in the acidic range.

Cyclization in accordance with process version (a) is conducted, for example, by dissolving the compounds of Formula IV in an inert, water immiscible solvent, such as benzene, toluene, xylene, chlorobenzene, anisole, mesitylene, and reacting with paraformaldehyde, optionally at an elevated temperature up to the boiling temperature of the solvent. Reaction with formaldehyde can also be carried out in an aqueous solution at room temperature and at a pH of 2–7, if the paraformaldehyde has been previously cleaved to formaldehyde in the presence of acids at an elevated temperature in an aqueous solution.

Cyclization can also take place with glyoxylic acid. In this process, the amine, dissolved in water or in an inert organic solvent, e.g., ethyl acetate, is combined suitably with an aqueous solution of glyoxylic acid at a pH of 0–7, preferably 4. The subsequent decarboxylation is effected at an elevated temperature, optionally at the boiling temperature of an above-mentioned inert solution, e.g., toluene or xylene.

A 1,2,3,4-tetrahydro-9H-pyrido[3,4-b]indole derivative is obtained during cyclization; this compound is subsequently dehydrogenated in both cases. Dehydrogenation can be performed, for example, by dissolving and/or suspending the starting material in an inert solvent, and adding elemental sulfur; the amount of the latter is dimensioned approximately so that one molar equivalent of sulfur is used per double bond. The reaction mixture is refluxed for several hours, the course of the reaction being monitored by thin-layer chromatography. Suitable for the dehydrogenation are all aprotic solvents, the boiling point of which ranges above 100° C. and which are inert with respect to the starting material, such as, for example, xylene, mesitylene, anisole, toluene, chlorobenzene, and diphenyl ether.

Another method is the dehydrogenation with noble metal catalysts, such as platinum in finely divided form, palladium black or palladium-carbon in xylene, mesitylene or cumene at 120°–180° C. and with reaction periods of 2–6 hours. Another preferred method is dehydrogenation with tert-butyl hypochlorite and tertiary bases, preferably in the range from −15° C. to room temperature (German Patent Application 35 04 045.9).

Splitting off of the benzyl group takes place, for example, by hydrogenation in the presence of a catalyst, such as, for example, of a noble metal catalyst, such as palladium on a suitable support, such as carbon, or with Raney nickel in protonic solvents, such as, for example, alcohols, under a hydrogen normal pressure or hydrogen elevated pressure. The reaction temperatures range from room temperature to the boiling temperature of the solvent, In general, the reaction is finished after 2–10 hours.

Etherification of the 5- or 6-hydroxy-β-carboline derivatives takes place, for example, in the presence of bases with a benzyl derivative of Formula V with a leaving group, such as , for example, a halogenide, tosylate, or mesylate, in polar solvents, e.g., dimethyl sulfoxide, dimethylformamide, acetonitrile, or ethanol at temperatures up to the boiling point of the solvent. Examples of suitable bases include: alkali compounds, such as, for example, sodium or potassium hydroxides, carbonates, alcoholates or hydrides, potassium fluoride, DBU, "DABCO", or ethyldiisopropylamine. It is also possible, if desired, to work in the presence of phase transfer catalysts, such as, for example, crown ethers, "Aliquat", tetrabutyl-ammonium hydrogen sulfate, or 2,2,2-cryptand. The reaction is suitably conducted under an inert gas atmosphere, for example under argon or nitrogen.

All conventional methods are suited for the interesterification according to process version (b), such as, for example, reaction with the corresponding alcohol or alkali alcoholate; if desired, titanium tetraisopropylate can be added as the catalyst, or in equimolar quantity up to an excess in the anyhydrous, corresponding alcohol. The interesterification is usually performed at temperatures of 60°–120° C. and is finished after about 2–6 hours. Basically, interesterifications are also possible with the following reagents: triphenylphosphine/azodicarboxylic acid ester or bromine tribromide/alcohol, or copper salts/alcohols, etc.

Introduction of the tert-butyl ester group can be effected, in particular, for example by reacting the carboxylic acid with tert-butoxybisdimethylaminomethane. In general, the reaction is performed under an inert gas atmosphere, such as argon or nitrogen, and with exclusion of moisture at an elevated temperature.

Saponification of the ester group can take place in an acidic or alkaline fashion; preferably an alkaline saponification is conducted by heating the ester to temperatures up to the reflux temperature of the reaction mixture with a dilute aqueous alkaline solution, such as, potassium or sodium hydroxide, in a protonic solvent, such as, for example, methanol, ethanol or ethylene glycol.

If racemates are obtained, splitting of the racemates can take place according to conventional methods.

All starting compounds are known or they can be routinely prepared from known starting materials using conventional methods. See e.g., U.S. Ser. No. 623,610 of Jun. 22, 1984, which is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

(A)

Under nitrogen, 6 g (43.5 millimoles) of finely pulverized potassium carbonate is stirred for 10 minutes at 95° C. in 25 ml of absolute dimethylformamide. Then, while the mixture is hot, 10 g (29.6 mmol) of 5-benzyl-oxy-3-(1-isopropylamino-2-methoxyethyl)indole is added and the mixture is stirred approximately 10 minutes at 95° C. until the compound has been dissolved. Thereupon, likewise at 95° C., a solution of 34.5 mmol of glycine anisaldehyde isopropyl ester in 25 ml of dimethylformamide is added dropwise in a time period of 30 minutes. The solution is agitated until the starting indole can no longer be detected in a thin-layer chromatogram. After cooling, the product is filtered off by suction from potassium carbonate and rinsed with toluene. After adding 100 ml of toluene, 200 ml of 1N hydrochloric acid is added and the mixture stirred for 3 hours at room temperature. The toluene phase is separated, and the aqueous acidic phase is extracted by shaking with 100 ml of toluene. The organic phase is discarded. The acidic phase is cooled to 5° C., combined with 100 ml of toluene, and adjusted to pH 10–12 with 4N sodium hydroxide solution. After extraction by shaking, the mixture is again extracted by shaking with 100 ml of toluene, and the combined organic phase is washed with 50 ml of water, dried, filtered, and concentrated, thus obtaining 70% 2-amino-3-(5-benzyloxyindol-3-yl)-4-methoxybutyric acid isopropyl ester as an oil.

(B)

A solution is prepared from 3.8 g of 2-amino-3-(5-benzyloxyindol-3-yl)-4-methoxybutyric acid isopropyl ester (10 mmol) in 80 ml of xylene and added dropwise to a suspension of 360 mg of paraformaldehyde in 60 ml of xylene heated for 45 minutes to 100° C. The mixture is then refluxed for 2 hours on a water trap. After concentration, the residue is chromatographed over silica gel with methylene chloride:acetone=1:1 as the eluent, yielding 2.5 g of 6-benzyloxy-4-methoxymethyl-1,2,3,4-tetrahydro-β-carboline-3-carboxylic acid isopropyl ester (65% yield as an oil); or a suspension of 2.56 g of paraformaldehyde in 8 ml of water and 0.8 ml of concentrated hydrochloric acid is refluxed at 80° C. for 1 hour. One-tenth of the thus-obtained clear solution is added dropwise, after cooling to room temperature, to a solution of 3.8 g (10 mmol) of 2-amino-3-(5-benzyloxyindol-3-yl)-4-methoxybutyric acid isopropyl ester in 500 ml of water and 10 ml of concentrated hydrochloric acid (pH=3). After ½ hour of agitation, an estimate of the amount of amino compound still remaining is made by thin-layer chromatography, and a corresponding quantity of formaldehyde solution is added. Thereupon, the mixture is stirred for another hour and then extracted twice by shaking with 50 ml of toluene, respectively. The organic phase is discarded. The aqueous phase is adjusted, after adding 100 ml of toluene, to a pH of 5.3 with 27% strength sodium hydroxide solution. After extraction by shaking, the mixture is additionally extracted by shaking twice with 50 ml of toluene; these 3 organic phases are combined, dried over sodium sulfate, filtered, and concentrated, thus obtaining 3.3 g (85%) of 6-benzyloxy-4-methoxymethyl-1,2,3,4-tetrahydro-β-carboline-3-carboxylic acid isopropyl ester as an oil.

(C)

A solution is prepared from 3.3 g (8.5 mmol) of 6-benzyloxy-4-methoxymethyl-1,2,3,4-tetrahydro-β-carboline-3-carboxylic acid isopropyl ester in 150 ml of methylene chloride, combined under argon with 3.9 ml of triethylamine, and cooled to −15° C. At this temperature, a solution of 3.2 ml (25.6 mmol) of tert-butyl hypochlorite in 50 ml of methylene chloride is added dropwise without delay to this solution. After the adding step is completed, the mixture is stirred for another 10 minutes, combined with 2.6 ml of triethylamine, and agitated for 2 hours at room temperature. Subsequently, the mixture is concentrated to one-half thereof and extracted once by shaking with dilute ammonia solution. The organic phase is dried, filtered, and concentrated. The residue is chromatographed over silica gel with methylene chloride:acetone =4:1 as the eluent. Recrystallization from ethyl acetate gives 1.1 g (35% yield) of 6-benzyloxy-4-methoxymethyl-β-carboline-3-carboxylic acid isopropyl ester, mp 150°–151° C.

EXAMPLE 2

(A)

At room temperature and under normal pressure, 7 g (18 mmol) of 6-benzyloxy-4-methoxymethyl-β-carboline-3-carboxylic acid isopropyl ester is hydrogenated in 600 ml of ethanol with 7 g of palladium/carbon (10%) as well as hydrogen for 8.5 hours. After the mixture has been removed from the catalyst by filtration, it is concentrated, thus obtaining 4.8 g (90% yield) of 6-hydroxy-4-methoxymethyl-β-carboline-3-carboxylic acid isopropyl ester which is further reacted without any additional purification.

A solution is prepared from 500 mg (1.6 mmol) of 6-hydroxy-4-methoxymethyl-β-carboline-3-carboxylic acid isopropyl ester in 50 ml of isopropanol, combined with 500 mg (3.6 mmol) of anhydrous, pulverized potassium carbonate, and stirred under argon for 10 minutes. Then 0.25 ml (1.99 mmol) of 2-chlorobenzyl chloride is added and the mixture refluxed for 2 hours. After suctioning off from the potassium carbonate, the filtrate is concentrated and separated over silica gel with methylene chloride:acetone=3:1 as the eluent, thus producing 172 mg of 6-(2-chlorobenzyloxy)-4-methoxymethyl-β-carboline-3-carboxylic acid isopropyl ester, mp 135°–141° C.

The following compounds are produced analogously:
6-(4-chlorobenzyloxy)-4-methoxymethyl-β-carboline-3-carboxylic acid isopropyl ester, mp 184°–185° C.;
6-(3-chlorobenzyloxy)-4-methoxymethyl-β-carboline-3-carboxylic acid isopropyl ester, mp 180°–183° C.;
6-(2-fluorobenzyloxy)-4-methoxymethyl-β-carboline-3-carboxylic acid isopropyl ester;
6-(3-fluorobenzyloxy)-4-methoxymethyl-β-carboline-3-carboxylic acid isopropyl ester, mp 168°–170° C.;
6-(3-methoxybenzyloxy)-4-methoxymethyl-β-carboline-3-carboxylic acid isopropyl ester, mp 160°–163° C.;
6-(4-cyanobenzyloxy)-4-methoxymethyl-β-carboline-3-carboxylic acid isopropyl ester, mp 218°–222° C.;
6-(4-bromobenzyloxy)-4-methoxymethyl-β-carboline-3-carboxylic acid isopropyl ester, mp 180°–190° C.;
6-(3-cyanobenzyloxy)-4-methoxymethyl-β-carboline-3-carboxylic acid isopropyl ester, mp 194°–200° C.;
6-(2-cyanobenzyloxy)-4-methoxymethyl-β-carboline-3-carboxylic acid isopropyl ester, mp 168°–172° C.;
6-(2-bromobenzyloxy)-4-methoxymethyl-β-carboline-3-carboxylic acid isopropyl ester, mp 148°–151° C.;
6-(4-fluorobenzyloxy)-4-methoxymethyl-β-carboline-3-carboxylic acid isopropyl ester, mp 160°–163° C.;
6-(2,4-dichlorobenzyloxy)-4-methoxymethyl-β-carboline-3-carboxylic acid isopropyl ester, mp 156°–159° C.;
6-(4-methylbenzyloxy)-4-methoxymethyl-β-carboline3-carboxylic acid isopropyl ester;
6-(3-methylbenzyloxy)-4-methoxymethyl-β-carboline-3-carboxylic acid isopropyl ester;
6-(2-methylbenzyloxy)-4-methoxymethyl-β-carboline-3-carboxylic acid isopropyl ester.

EXAMPLE 3

1.4 g (3.6 mmol) of 6-benzyloxy-4-methoxymethyl-β-carboline-3-carboxylic acid ethyl ester is boiled under reflux for 2 hours in 100 ml of isopropanol with 0.7 ml (2.2 mmol) of titanium tetraisopropoxide. After concentration, the mixture is taken up in 80 ml of 1N hydrochloric acid and extracted by shaking with 250 ml of ethyl acetate. The ethyl acetate phase is washed with a small amount of water, dried, filtered, and concentrated. After chromatography over silica gel with methylene chloride:acetone=4:1 as the eluent, the 6-benzyloxy-4-methoxymethyl-β-carboline-3-carboxylic acid isopropyl ester, mp 150°–151° C., is obtained in an 80% yield.

The following compounds are produced in a basically analogous way, except for using the corresponding alcohol:
6-benzyloxy-4-methoxymethyl-β-carboline-3-carboxylic acid cyclopentyl ester;
6-benzyloxy-4-methoxymethyl-β-carboline-3-carboxylic acid methylcyclopropyl ester;
6-benzyloxy-4-methoxymethyl-β-carboline-3-carboxylic acid cyclohexyl ester, mp 177° C.;
6-(3-fluorobenzyloxy)-4-methoxymethyl-β-carboline-3-carboxylic acid 2-butyl ester, mp 145° C.;
6-benzyloxy-4-methoxymethyl-β-carboline-3-carboxylic acid neopentyl ester, mp 192° C.;
6-benzyloxy-4-methoxymethyl-β-carboline-3-carboxylic acid isobutyl ester, mp 157°–161° C.;
6-benzyloxy-4-methoxymethyl-β-carboline-3-carboxylic acid 2-butyl ester, mp 119°–123° C.

EXAMPLE 4

One gram of 6-benzyloxy-4-methoxymethyl-β-carboline-3-carboxylic acid is heated in 10 ml of aminal ester for 3.5 hours to a bath temperature of 120° C. After evaporation, the residue is chromatographed over silica gel with hexane:acetone=13:7 as the eluent, thus obtaining 300 mg of 6-benzyloxy-4-methoxymethyl-β-carboline-3-carboxylic acid tert-butyl ester.

The following compound is prepared analogously:
6-(4-fluorobenzyloxy)-4-methoxymethyl-β-carboline-3-carboxylic acid tert-butyl ester, mp 160°–167° C.

EXAMPLE 5

(A)

Under argon, 78.1 g of 5-benzyloxy-4-methoxy-methyl-β-carboline-3-carboxylic acid ethyl ester is suspended in 1 liter of isopropanol, combined with 28 ml of titanium tetraisoproxide and heated under reflux for 4 hours. After cooling, evaporation, and chromatography over silica gel with hexane:acetone=1:2 as the eluent, impurities are separated. While making the transition to hexane:acetone=1:3 and hexane:isopropanol=3.5:1, 56.1 g of 5-Benzyloxy-4-methoxymethyl-β-carboline-3-carboxylic acid isopropyl ester, mp 208°–209° C., is isolated.

The following compounds are prepared in an analogous fashion:
5-(3-chlorobenzyloxy)-4-methoxymethyl-β-carboline-3-carboxylic acid isopropyl ester, mp 173°–174° C.;
5-(3-fluorobenzyloxy)-4-methoxymethyl-β-carboline-3-carboxylic acid isopropyl ester, mp 181°–182° C.;
5-(2-fluorobenzyloxy)-4-methoxymethyl-β-carboline-3-carboxylic acid isopropyl ester, mp 145°–146° C.;
5-(4-chlorobenzyloxy)-4-methoxymethyl-β-carboline-3-carboxylic acid isopropyl ester, mp 212°–213° C.;
5-(2-chlorobenzyloxy)-4-methoxymethyl-β-carboline-3-carboxylic acid isopropyl ester, mp 198°–199° C.;
5-(4-fluorobenzyloxy)-4-methoxymethyl-β-carboline-3-carboxylic acid isopropyl ester;
5-(3-methylbenzyloxy)-4-methoxymethyl-β-carboline-3-carboxylic acid isopropyl ester.

In a way basically analogous to (A), the following compounds were prepared, using the corresponding alcohols:
5-benzyloxy-4-methoxymethyl-β-carboline-3-carboxylic acid cyclohexyl ester, mp 143°–145° C.;
5-benzyloxy-4-methoxymethyl-β-carboline-3-carboxylic acid hexafluoroisopropyl ester;
5-benzyloxy-4-methoxymethyl-β-carboline-3-carboxylic acid methylcyclopropyl ester;
5-benzyloxy-4-methoxymethyl-β-carboline-3-carboxylic acid isobutyl ester;
5-(4-chlorobenzyloxy)-4-methoxymethyl-β-carboline-3-carboxylic acid cyclopentyl ester.

(B)
740 mg (2 mmol) of 5-benzyloxy-4-methoxymethyl-β-carboline-3-carboxylic acid is stirred for 2 hours at 80° C. in 50 ml of ethanol and 20 ml of water with 977 mg of cesium carbonate. After concentration on a rotary evaporator and drying in a desiccator, the mixture is taken up in 50 ml of DMF, combined with 0.2 ml of 2-bromopropane, and heated for 8 hours to 60°–70° C. After concentration, the mixture is chromatographed over silica gel with hexane:acetone=1:1 as the eluent, thus obtaining 340 mg of 5-benzyloxy-4-methoxymethyl-β-carboline-3-carboxylic acid isopropyl ester having the above-mentioned melting point.

The following compounds are prepared analogously:
5-(3-chlorobenzyloxy)-4-methoxymethyl-β-carboline-3-carboxylic acid cyclobutyl ester, mp 166°–167° C.;
5-(3-chlorobenzyloxy)-4-methoxymethyl-β-carboline-3-carboxylic acid cyclopropyl ester, mp 167°–178° C.;
5-(3-chlorobenzyloxy)-4-methoxymethyl-β-carboline-3-carboxylic acid isobutyl ester.

EXAMPLE 6

500 mg of 5-benzyloxy-4-methoxymethyl-β-carboline-3-carboxylic acid is heated with 5 ml of aminal ester for 3.5 hours to a bath temperature of 120° C. After evaporation to dryness, the residue is chromatographed over silica gel with hexane:acetone=13:7 as the eluent. Yield: 190 mg of 5-benzyloxy-4-methoxymethyl-β-carboline-3-carboxylic acid tert-butyl ester, mp 180°–181° C.

The following compound is produced analogously:
5-(3-benzyloxy)-4-methoxymethyl-β-carboline-3-carboxylic acid tert-butyl ester.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating a sleep disturbance, comprising administering an effective amount of a compound of the formula

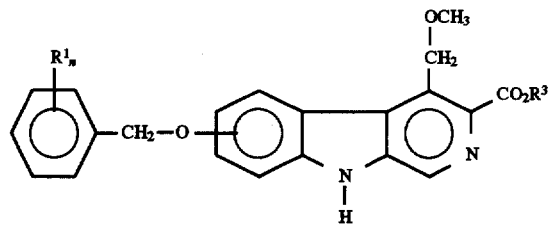

wherein $R^1_n$ is halogen, lower alkyl, or lower alkoxy, $R^3$ is branched $C_{3-6}$-alkyl, branched $C_{3-6}$-alkyl substituted by halogen, $C_{3-6}$ cycloalkyl, or $C_{3-6}$-cycloalkyl substituted by methyl, n is 0–5 and the $R^1$ benzyloxy group is in the 5- or 6-position.

2. A method of claim 1 wherein n=0.
3. A method of claim 1 wherein n=1.
4. A method of claim 1 wherein n=2.
5. A method of achieving a psychotropic effect comprising administering an effective amount of a compound of the formula

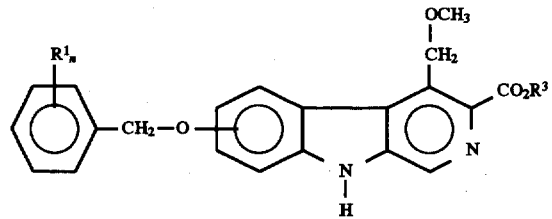

wherein $R^1_n$ is halogen, lower alkyl, or lower alkoxy, $R^3$ is branched $C_{3-6}$-alkyl, branched $C_{3-6}$-alkyl substituted by halogen, $C_{3-6}$ cycloalkyl, or $C_{3-6}$-cycloalkyl substituted by methyl, n is 0–5 and the $R^1$ benzyloxy group is in the 5- or 6-position.

6. A method for achieving a psychotropic effect comprising administering 6-benzyloxy-4-methoxymethyl-β-carboline-3-carboxylic acid isopropyl ester.

7. A method of treating epilepsy or a sleep disturbance, comprising administering an effective amount of 6-benzyloxy-4-methoxymethyl-β-carboline-3-carboxylic acid isopropyl ester.

8. A pharmaceutical composition comprising an amount of the compound 6-benzyloxy-4-methoxymethyl-β-carboline-3-carboxylic acid isopropyl ester effective for achieving a psychotropic effect and a pharmaceutically acceptable carrier.

9. A pharmaceutical composition comprising a therapeutically effective amount in the range of 0.05–100 mg of the compound 6-benzyloxy-4-methoxymethyl-β-carboline-3-carboxylic acid isopropyl ester and a pharmaceutically acceptable carrier.

* * * * *